United States Patent
Wattanakit et al.

(10) Patent No.: US 11,801,499 B2
(45) Date of Patent: Oct. 31, 2023

(54) CATALYST FOR PRODUCING LIGHT OLEFINS FROM C4-C7 HYDROCARBONS

(71) Applicant: PTT Global Chemical Public Company Limited, Bangkok (TH)

(72) Inventors: Chularat Wattanakit, Bangkok (TH); Chadatip Rodaum, Ratchaburi (TH); Anawat Thivasasith, Nakhon Ratchasima (TH); Sitthiphong Pengpanich, Bangkok (TH)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 204 days.

(21) Appl. No.: 17/359,360

(22) Filed: Jun. 25, 2021

(65) Prior Publication Data

US 2021/0322961 A1    Oct. 21, 2021

Related U.S. Application Data

(63) Continuation of application No. PCT/TH2019/000063, filed on Dec. 3, 2019.

(51) Int. Cl.

| | | |
|---|---|---|
| *C07C 4/06* | (2006.01) | |
| *B01J 29/40* | (2006.01) | |
| *B01J 21/04* | (2006.01) | |
| *B01J 21/10* | (2006.01) | |
| *B01J 35/00* | (2006.01) | |
| *B01J 29/04* | (2006.01) | |
| *B01J 21/16* | (2006.01) | |
| *C10G 11/04* | (2006.01) | |
| *B01J 35/06* | (2006.01) | |
| *C10G 11/06* | (2006.01) | |
| *C10G 11/08* | (2006.01) | |

(52) U.S. Cl.
CPC ............... *B01J 29/40* (2013.01); *B01J 21/04* (2013.01); *B01J 21/10* (2013.01); *B01J 21/16* (2013.01); *B01J 29/041* (2013.01); *B01J 35/0006* (2013.01); *B01J 35/0046* (2013.01); *B01J 35/06* (2013.01); *C07C 4/06* (2013.01); *C10G 11/04* (2013.01); *C10G 11/06* (2013.01); *C10G 11/08* (2013.01); *B01J 2229/186* (2013.01); *C07C 2529/04* (2013.01); *C07C 2529/06* (2013.01); *C07C 2529/08* (2013.01); *C07C 2529/18* (2013.01); *C07C 2529/40* (2013.01); *C07C 2529/65* (2013.01); *C07C 2529/70* (2013.01)

(58) Field of Classification Search
CPC ... B01J 21/04; B01J 21/10; B01J 21/16; B01J 29/041; B01J 29/40; B01J 29/08; B01J 29/18; B01J 29/65; B01J 29/7007; B01J 35/06; B01J 35/08; B01J 35/002; B01J 35/023; B01J 35/0013; B01J 35/1057; B01J 35/1061; B01J 35/1066; B01J 35/1095; B01J 37/035; B01J 2229/186; C10G 11/04; C10G 11/06; C10G 11/08; C10G 2400/20; C10G 11/05; C07C 4/06; C07C 2529/04; C07C 2529/06; C07C 2529/08; C07C 2529/18; C07C 2529/65; C07C 2529/70; C07C 2529/40
USPC ........ 502/60, 63, 64, 68, 69, 71, 77, 78, 79, 502/80, 84; 208/113, 118, 119, 121, 122; 585/648, 650, 651, 653
See application file for complete search history.

(56) References Cited

U.S. PATENT DOCUMENTS

| | | |
|---|---|---|
| 6,222,087 B1 | 4/2001 | Johnson et al. |
| 7,981,273 B2 | 7/2011 | Nicholas et al. |
| 8,157,985 B2 | 4/2012 | Nicholas et al. |
| 2005/0070422 A1 | 3/2005 | Chen et al. |
| 2010/0105974 A1 | 4/2010 | Towler et al. |
| 2018/0197400 A1 | 7/2018 | Pan et al. |

FOREIGN PATENT DOCUMENTS

| | | | |
|---|---|---|---|
| JP | 4157946 B2 | | 7/2008 |
| WO | 2017009664 A1 | | 1/2017 |
| WO | WO 2017/009666 | * | 1/2017 |
| WO | 2018108544 A1 | | 6/2018 |
| WO | 2018157042 A1 | | 8/2018 |

OTHER PUBLICATIONS

Liu et al., Hierarchical Macro-meso-microporous ZSM-5 Zeolite Hollow Fibers with Highly Efficient Catalytic Cracking Capability, Scientific Reports, vol. 4, No. 7276, Dec. 2, 2014, retrieved from the Internet: <URL: https://www.nature.com/articles/srep07276>, pp. 1-6.
International Search Report and Written Opinion dated May 5, 2020 in connection with International Application No. PCT/TH2019/000063, 8 pages.

* cited by examiner

*Primary Examiner* — Elizabeth D Wood
(74) *Attorney, Agent, or Firm* — Baker & McKenzie LLP

(57) ABSTRACT

The present invention relates to a catalyst for producing light olefins from C4-C7 hydrocarbons from catalytic cracking reaction and the production process of light olefins from said catalyst, wherein said catalyst has core-shell structure comprising a zeolite core with mole ratio of silicon to aluminium (Si/Al) between 2 to 250 and layered double hydroxide shell (LDH). The catalyst according to the invention provides high percent conversion of substrate to products and high selectivity to light olefins product.

18 Claims, 4 Drawing Sheets

CATALYST FOR PRODUCING LIGHT OLEFINS FROM C4-C7 HYDROCARBONS

CROSS-REFERENCE TO RELATED APPLICATIONS

This application is a continuation of and claims priority to International Application No. PCT/TH2019/000063, filed on Dec. 3, 2019, titled "Catalyst for Producing Light Olefins From C4-C7 Hydrocarbons," which claims priority to Thailand Application No. 1801008085 filed on Dec. 26, 2018, both of which are incorporated by reference in their entirety for all purposes.

FIELD OF THE INVENTION

Chemistry relates to the catalyst for producing light olefins from C4-C7 hydrocarbons.

BACKGROUND OF THE INVENTION

Light olefins such as ethylene and propylene are the important petrochemical precursors in the production of important polymers such as polyethylene, polypropylene and etc. At present, the industrial production of light olefins uses the molecular decomposition of naphtha or ethane separated from natural gas by thermal steam cracking as main process. Said process require high temperature which consumes high energy and also causes a large amount of accumulated coking in the system. Therefore, the process has to be stopped for maintenance quite often. The production of light olefins by catalytic cracking of naphtha compounds is the alternative process in order to increase yield of light olefins using low reaction temperature and reducing accumulated coking in the system.

Up to present, there have been reports about the technologies for the production of olefins by catalytic cracking of naphtha compounds. For example, the researchers from Honeywell UOP LLC (U.S. Pat. No. 7,981,273B2, 8,157, 985B2, and US20100105974A1) had developed the aluminosilicate or zeolite catalysts by adding potassium, sodium, organoammonium cation compounds, and gallium for the catalytic cracking of hydrocarbon compound including naphtha compounds into olefin compounds wherein the organoammonium cation compounds had many types such as ethyl trimethyl ammonium (ETMA), diethyl dimethyl ammonium (DEDMA), and tetraethylammonium (TEA), etc. Also, there has been the development of catalysts from the mixing of different types of catalysts, wherein the first group used zeolites such as chabazite, erionite, ferrierite, and ZSM-22, etc. were mixed with the second group such as nano-silicalite in which the ratio of silica to alumina was more than 200.

Moreover, the researchers from ExxonMobil Oil Corporation (U.S. Pat. No. 6,222,087B1 and US20050070422A1) had studied and developed the catalysts for the production of light olefins from the catalytic cracking of C4-C7 hydrocarbons, wherein the studied catalysts were zeolites such as ZSM-22, ZSM-35, SAPO-34, ZSM-5, and ZSM-11 including zeolites having the ratio of silicon to aluminium more than 300. Furthermore, there was a mix-up of phosphorous and metal oxide such as gallium, titanium, and zirconia in order to increase yield of propylene compound.

In order to produce light olefins by catalytic cracking at highest efficiency, the used catalyst must provide the highest selectivity of light olefins products when comparing to the side reactions especially light alkane products such as methane, ethane, and propane. Therefore, there has been the development of catalysts used in said processes continuously for both providing the highest selectivity of light olefins products and the development of catalysts in order to reduce the catalyst deactivation, etc.

The development of catalysts for the production of light olefins by catalytic cracking of hydrocarbon compounds with zeolite catalyst are interesting. The zeolite compound is the crystalline aluminosilicate which is one catalyst that can be applied for various applications in petroleum and petrochemical industries such as adsorbent, ion exchanger, and heterogeneous catalysts that can used as the catalyst or support. The outstanding properties of zeolite are an adjustable pH to the nature of applied reaction, thermal and chemicals stabilities, and shape selectivity. Hence, said catalyst which comprises the suitable Brønsted acid site and pores that have the specific properties to the selectivity of the desired light olefins products can be applied.

Nevertheless, the use of conventional zeolites in the industry still has limitations such as low catalytic efficiency, fast degeneration, and a difficult and complicated process for regenerating a catalyst. The main factors that cause limitations to said conventional zeolites are the mass transfer and diffusion limit which result from the pore size in the zeolite structure which is very small (angstrom scale) in the large zeolite crystallize structure which causes the critical mass transfer. This makes difficulty to the reaction of the precursor at the active sites and may cause the catalyst deactivation because of the high amount of coke formation from the recombination reactions of the intermediates. Moreover, there are limitations of the use of the conventional zeolites in the production process of light olefins by catalytic cracking of hydrocarbon compounds in order to obtain high selectivity of light olefins products from other reasons such as side reactions at the active sites which are on the outside surface.

WO2018157042 discloses the catalyst composition with core-shell structure and the preparation process of said catalyst, wherein the core and shell materials were mesoporous material in which the core comprising at least one material selected from TS-1, silicalite, silicalite-1, BETA, ZSM-5, AlPO-5, MCM-41, and SAPO and further comprising metals such as platinum, gold, palladium, copper, nickel, iron, cobalt, ruthenium, antimony, bismuth, or metal oxides. The shell comprised at least one material selected from microporous zeolite, porous silica, alumina, titanium oxide, zirconium dioxide, carbon, metal organic framework (MOF), zeolitic imidazolate framework (ZIF), or covalent organic framework (COF). However, this study had not reported the application of said catalyst in the production process of light olefins.

WO2018108544 discloses the catalyst compositions used in the production process of light olefins from propane, wherein said catalyst comprising 2 compositions that were physically mixed. The first composition comprised the solid support in layered double hydroxide form selected from aluminium dioxide, silicon dioxide, zirconium dioxide, titanium dioxide, magnesium oxide, calcium oxide, or mixtures thereof with the dehydrogenation active metal such as platinum. The second part comprised the inorganic support selected from aluminum oxide, silicon dioxide, zirconium dioxide, titanium dioxide, zeolite, or mixtures thereof with a transition metal selected from molybdenum, tungsten, rhenium, or mixtures thereof as co-compositions.

WO2017009664A1 discloses the character of the catalyst with core-shell structure and the preparation process of said catalyst. The core material was silicate, aluminium silicate, vanadium silicate, iron silicate, silicon-aluminium phosphate (SAPO), or aluminium phosphate (AlPO). The shell material was layered double hydroxide. However, said patent did not mention the application of said catalyst in any production process.

From the reasons mentioned above, this invention aims to prepare the catalyst for the production of light olefins from the C4-C7 hydrocarbons from the catalytic cracking and the production process of light olefins using said catalyst, wherein said catalyst has a core-shell structure comprising zeolite core and layered double hydroxide shell in order to be suitable for the application in the production of light olefins with high selectivity of light olefins, small amounts of by-products such as methane, ethane, and propane, and increasing the stability of the catalytic reaction. Moreover, said catalyst provides good production efficiency of light olefins comparing to the previous studies without any further metal compositions added.

SUMMARY OF INVENTION

The present invention relates to the catalyst for producing light olefins from C4-C7 hydrocarbons from catalytic cracking and the production process of light olefins from said catalyst, wherein said catalyst has a core-shell structure comprising zeolite core with mole ratio of silicon to aluminium (Si/Al) between 2 to 250, and layered double hydroxide shell (LDH).

DETAILED DESCRIPTION OF THE INVENTION

Figure 1:
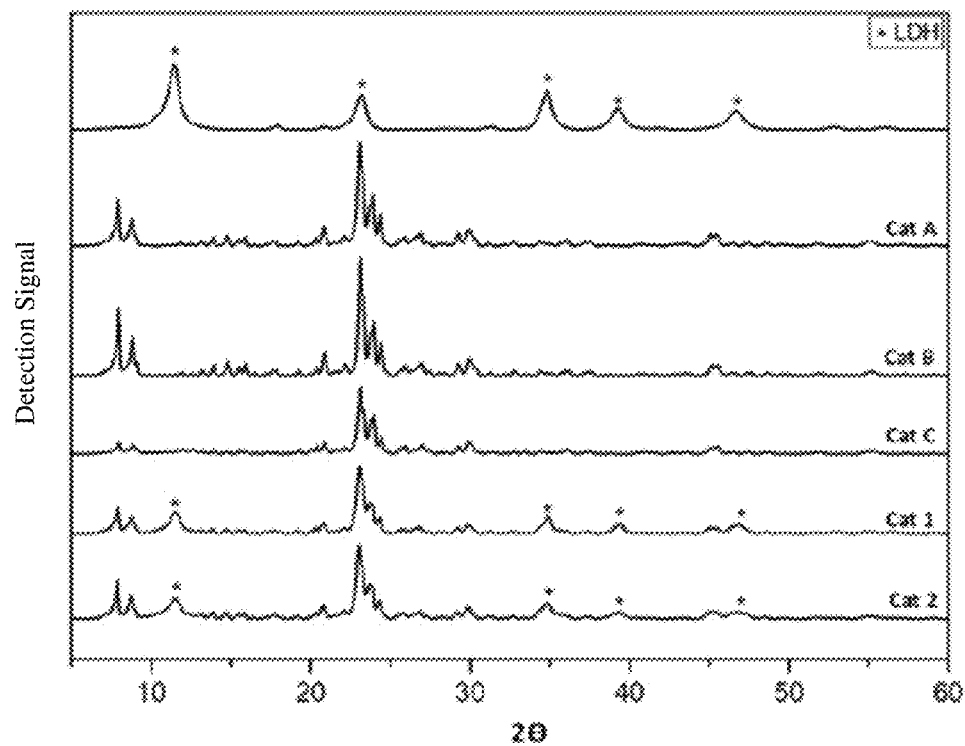
FIG. 1 shows the crystal characters of the samples according to the invention and the comparative samples.

The present invention relates to the catalyst for producing light olefins from C4-C7 hydrocarbons which will be described according to the following embodiments.

Any aspect that being described here is meant to include the application to the other aspects of this invention, unless stated otherwise.

Technical terms or scientific terms used here have definitions as by person skilled in the art unless stated otherwise.

Any tools, equipment, methods, or chemicals named here mean tools, equipment, methods, or chemicals being used commonly by person skilled in the art unless stated otherwise that they are tools, equipment, methods, or chemicals specific only in this invention.

Use of singular noun or singular pronoun with "comprising" in claims or specification means "one" and including "one or more", "at least one", and "one or more than one" too.

All compositions and/or methods disclosed and claims in this application aim to cover embodiments from any action, performance, modification, or adjustment without any experiment that significantly different from this invention, and obtain with object with utility and resulted as same as the present embodiment according to person ordinary skilled in the art although without specifically stated in claims. Therefore, substitutable or similar object to the present embodiment, including any little modification or adjustment that clearly seen by person skilled in the art should be construed as remains in spirit, scope, and concept of invention as appeared in appended claims.

Throughout this application, term "about" means any number that appeared or showed here that could be varied or deviated from any error of equipment, method, or personal using said equipment or method.

Hereafter, invention embodiments are shown without any purpose to limit any scope of the invention.

This invention relates to the catalyst for producing light olefins from C4-C7 hydrocarbons from the catalytic cracking and the production process of olefins using said catalyst, wherein said catalyst has core-shell structure comprising zeolite core with mole ratio of silicon to aluminium between 2 to 30, and layered double hydroxide shell.

In one embodiment, the zeolite core is the hierarchical zeolite comprising a micropore with size between 0.3 to 0.6 nm, a mesopore with size between 2 to 10 nm, and a macropore with size more than 50 nm, wherein the mesopore and macropore proportions are 15 to 60% or more based in total pore volume.

In one embodiment, the mole ratio of silicon to aluminium of said zeolite is between 2 to 250. Preferably, the mole ratio of silicon to aluminium of said zeolite is between 15 to 30. Most preferably, the mole ratio of silicon to aluminium of said zeolite is 15.

In one embodiment, said zeolite is selected from ZSM-5 FAU MOR BETA or FER zeolite, preferably is ZSM-5.

In one embodiment, the crystal size of said zeolite is between 100 to 3,000 nm.

In one embodiment, the layered double hydroxide comprising the group 2 metals and the group 3 metals as the main compositions, preferably are magnesium (Mg) and aluminium (Al).

In one embodiment, the mole ratio of magnesium to aluminium of said layered double hydroxide is between 1 to 3. Preferably, the mole ratio is between 1 to 2.

In one embodiment, the thickness of said layered double hydroxide is between 100 to 1,000 nm.

Preferably, the catalyst according to the invention comprising hierarchical zeolite core and layered double hydroxide shell which comprising magnesium and aluminium, wherein said catalyst has a mass ratio of shell to core between 1:1 to 1:7, preferably is 1:2 to 1:6.

In another embodiment, the catalyst according to the invention has been improved in its property for the production of light olefins such as the product selectivity, the production yield, and the conversion from precursor to light olefins product, also comprising IIA, IIIA, VA, IIB, IIIB, VIB, and VIII metal group according to the periodic table of elements, which may be selected from but not limited to lanthanum, strontium, palladium, phosphorus, platinum, gallium, or zinc.

In one embodiment, the catalyst according to the invention may be prepared according to the following steps:
(a) preparing a solution comprising a compound for the preparation of zeolite and a soft template;
(b) subjecting the mixture obtained from step (a) to the hydrothermal process at the determined temperature and time in order to convert said mixture into the hierarchical zeolite;
(c) preparing a solution comprising a compound for preparing layered double hydroxide shell;
(d) preparing the solution comprising the zeolite obtained from step (b) and sodium carbonate;
(e) dropping the solution prepared from step (c) onto the solution prepared from step (d) while controlling pH of the solution;
(f) stirring the mixture obtained from step (e) for about 1 hour and washing with deionized water under stirring condition continuously for about another 1 hour, then washing with acetone under stirring condition continuously for about 10 to 14 hours;
(g) centrifuging the mixture washed with acetone obtained from step (f) in order to separate the synthesized catalyst;
(h) drying the catalyst obtained from step (g); and
(i) contacting the obtained sample with ammonium nitrate ($NH_4NO_3$) solution by ion exchange method using 100 mL of ammonium nitrate solution to 1 g of the catalyst at the temperature of 80° C. for about 2 hours, then drying and repeating 3 times, and finally calcining at the temperature of 550° C. for about 6 to 8 hours.

characterized in that the soft template in step (a) is a quaternary ammonium salt that may be selected from but not limited to tetraalkyl ammonium salt selected from tetrapropylammonium hydroxide and tetrabutylammonium hydroxide.

In one embodiment, the compound used for preparing zeolite is a mixture of the alumina compound selected from aluminum isopropoxide, sodium aluminate, or aluminium sulfate, and the silica compound selected from tetraethyl orthosilicate, sodium silicate, or silica gel.

In one embodiment, step (b) is operated at the temperature between 130 to 180° C.

In another embodiment, the preparation process of the catalyst according to the invention may further comprising the drying and calcining steps.

Drying may be performed by normal drying using oven, vacuum drying, stirred drying, and rotary evaporator.

Calcination may be performed under atmospheric condition for about 4 to 10 hours and temperature between about 350 to 650° C., preferably is for about 5 to 6 hours and temperature between about 350 to 400° C.

In another embodiment, the present invention relates to the use of the catalyst according to the invention in the production process of light olefins from catalytic cracking of C4-C7 hydrocarbons.

In one embodiment, the catalytic cracking of C4-C7 hydrocarbons may be occurred wherein the feeding of C4-C7 hydrocarbons is contacted with the catalyst according to the invention at the suitable conditions for the reaction which may be operated in fixed bed system.

The catalytic cracking of C4-C7 hydrocarbons may be occurred at the temperature between about 450 to 650° C., preferably is between about 550 to 600° C. under atmospheric pressure to 5 bars, most preferably is at the atmospheric pressure.

In one embodiment, the C4-C7 hydrocarbons is selected from butane, pentane, hexane, or heptane, preferably is pentane.

In one embodiment, the product obtained from the catalytic cracking of C4-C7 hydrocarbons using said catalyst is the light olefins, preferably are ethylene and propylene.

The weight hourly space velocity (WHSV) of the feeding of the hydrocarbon compound in the catalytic cracking is between about 1 to 50 hours$^{-1}$, preferably is between about 2 to 7 hours$^{-1}$.

Normally, the persons skilled in the art can modify the reaction conditions of the catalytic cracking of C4-C7 hydrocarbons to be suitable for type and composition of the feeding, the catalyst, and the reactor system.

The following example is only for demonstrating the embodiments of this invention, not for limiting the scope of this invention in any way.

Preparation of the Catalyst

The preparation of the catalyst can be performed according to the following methods.

Preparation of the Zeolite Core

The solution comprising sodium aluminate and tetraethyl orthosilicate was prepared, wherein the mole ratio of silicon to aluminum was 15. Tetrapropyl ammonium hydroxide was used as the template of zeolite. Then, the obtained mixture was subjected to hydrothermal process at the temperature about 130-180° C. for about 2 to 4 days in order to convert said mixture into zeolite.

Then, the obtained zeolite was washed with deionized water until the pH was lower than 9. The obtained substance was dried at the temperature about 100 to 120° C. for about 12 to 24 hours. Then, the calcination was performed in order to remove the template at the temperature about 500 to 650° C. for about 8 to 12 hours. The hierarchical zeolite was obtained as white powder.

Preparation of Layered Double Hydroxide Shell

The precursor solution of the layered double hydroxide comprising 2.4 to 4.8 mmol of magnesium nitrate and 1.2 to 2.4 mmol of aluminium nitrate was prepared. Then, the prepared solution was dropped onto the mixture comprising 0.2 to 0.5 g of sodium carbonate and 0.5 g of determined type of zeolite. The pH was controlled to be about 10.

Then, said mixture was stirred for about 1 hour and washed with deionized water. Then, acetone was added and stirred for 10 to 14 hours. Finally, the mixture was dried in vacuum oven according to the method disclosed by Chunping et al. (Chemical Science, 2016, 7(2), 1457-61).

Then, the ion exchange was performed on the catalyst of the mixture material of zeolite and layered double hydroxide synthesized from sodium ion into proton ion by ion exchanged method. The obtained catalyst of the mixture material of zeolite and layered double hydroxide was dissolved in 0.1 molar of ammonium nitrate ($NH_4NO_3$) solution at the temperature about 80° C., stirred for about 2 hours, and washed with pure water. The obtained zeolite was dried. Then, the obtained zeolite was calcined in order to remove contaminants at the temperature about 350° C. for about 6 hours.

Comparative Sample Cat A (Com ZSM5)

The ZSM-5 nano-zeolite having mole ratio of silicon to alumina of 15 that was commercially available was used as the comparative sample Cat A.

Comparative Sample Cat B (ZSM5)

The sample according to the invention Cat B was prepared by the method described in the preparation of the zeolite core above.

Comparative Sample Cat C (ComZSM5-Mg—Al(imp))

The comparative sample Cat C was prepared by contacting the comparative sample A with the magnesium and aluminium salt solution by impregnation method using 10 mL of magnesium nitrate and aluminium nitrate at the concentration from 0.4 to 1 molar at the temperature of 80° C. for 1 to 3 hours. Then, it was dried by rotary evaporator and dried in oven at the temperature of 100° C. for 24 hours. Then, sample was calcined at the temperature of 350° C. for 6 hours.

Sample According to the Invention Cat 1 (ComZSM5-LDH(ex))

The sample according to the invention Cat 1 was prepared by subjecting the comparative sample Cat A as core and prepared by the preparation method of catalyst according to the invention as described above in order to obtain the catalyst having zeolite core and layered double hydroxide shell.

Sample According to the Invention Cat 2 (ZSM5-LDH(ex))

The sample according to the invention Cat 2 was prepared by subjecting the comparative sample Cat B as core and prepared by the preparation method of catalyst according to the invention as described above in order to obtain the catalyst having zeolite core and layered double hydroxide shell.

Testing of Catalytic Cracking of C4-C7 Hydrocarbons for Producing Light Olefins Product The testing of catalytic cracking of C4-C7 hydrocarbons for the production of light olefins might be performed in the following conditions.

The catalytic cracking was operated in fixed-bed reactor by using about 0.2 to 0.4 g of catalyst. Before the reaction, the catalyst was contacted with nitrogen gas with flow rate about 10 to 50 ml/min for about 1 to 3 hours. Then, the C5 hydrocarbon compound was fed at the flow rate about 1.25 g/h. The reaction was continued at the temperature about 500 to 600° C. at the atmospheric pressure and the weight hourly space velocity (WHSV) was about 2 to 5 $hour^{-1}$.

Then, the reaction was monitored by measuring the changes of precursor and the formations of other compositions after reacted with the catalyst at any time using gas chromatography connected to the output of the fixed-bed reactor using flame ionization detector (FID) as the detector, and GASPRO capillary column for the analysis of each composition of said substance.

FIG. 1 shows the crystal characters of the samples according to the invention and the comparative samples that show the core and shell structure of zeolite and layered double hydroxide of the samples according to the invention Cat 1 and Cat 2.

Figure 2:
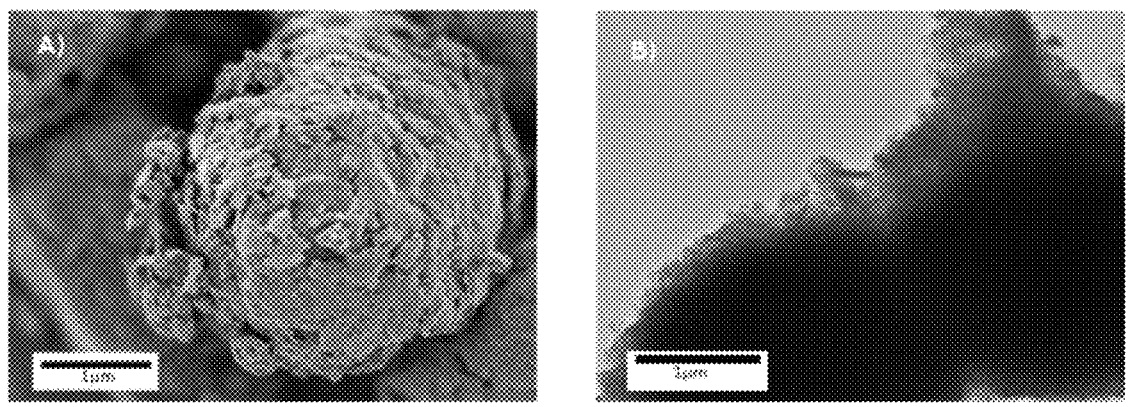
FIGS. 2 A) and B) show the results from the electron scanning microscope and the electron transmission microscope of the sample according to the invention Cat 2.

Furthermore, in order to show the crystal characters, the scanning electron microscope (SEM) and transmission electron microscopy (TEM) were employed. The results were showed in FIG. 2, which demonstrate that the zeolite according to the invention was hierarchical zeolite with the crystal size about 100 to 3,000 nm. From the test of a specific surface area of the micropore, mesopore, and macropore, it was found that both catalyst Cat A and Cat B had the size distribution of micropore, mesopore, and macropore, wherein the proportion of mesopore and macropore were greater than or equal to 15 to 60% when comparing to the total pore volume. Moreover, the hierarchical factor (HF) of the catalyst Cat A and Cat B was about 0.04. This shows that both catalysts had the hierarchical structure. The hierarchical factor can be calculated from the following equation.

$$\text{Hierarchical factor (HF)} = \text{Micropore volume } (V\text{micro})(cm^3/g)/\text{Total pore volume } (V\text{total})(cm^3/g) \times \text{Specific external surface area } (S\text{ext})(m^2/g)/\text{Specific surface area } (S\text{BET})(m^2/g)$$

Figure 3:
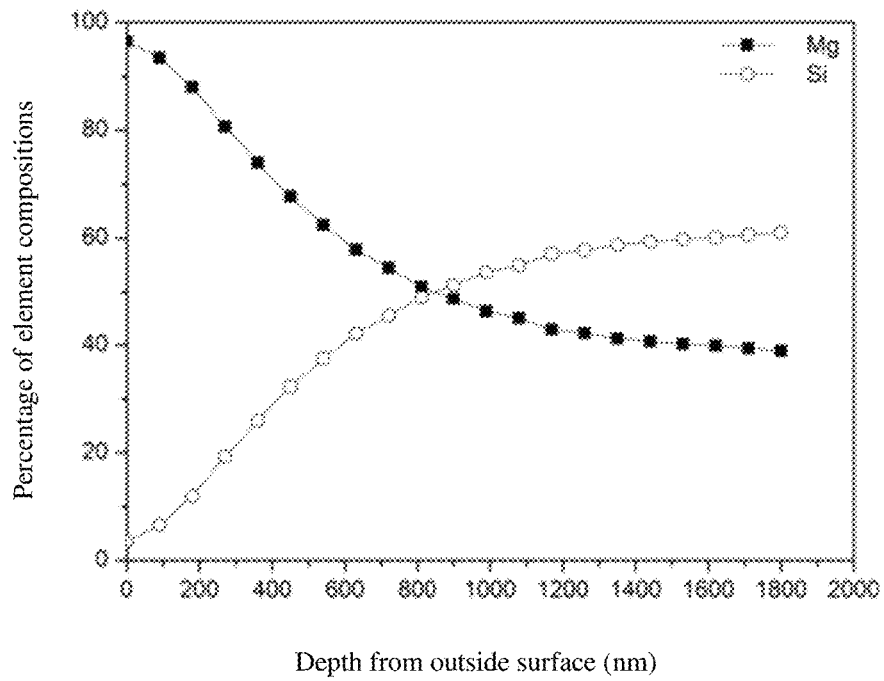
FIG. 3 shows the composition percentage of the elements changed according to the crystal size by the X-ray photoelectron spectroscopy (XPS) for the sample according to the invention Cat 2.

Hence, in order to confirm the core-shell structure of zeolite and layered double hydroxide of the samples according to the invention, the percentage concentration of magnesium and silicon that changed according to the crystal size were analyzed by X-ray photoelectron spectroscopy (XPS). The results were shown in FIG. 3.

In order to study the effect of the catalyst containing the hierarchical zeolite core and the layered double hydroxide shell to the production efficiency of light olefins from catalytic cracking of C4-C7 hydrocarbons, the catalysts according to the invention were studied with the comparative samples. The results were shown in FIG. 4 to FIG. 7.

Figure 4:
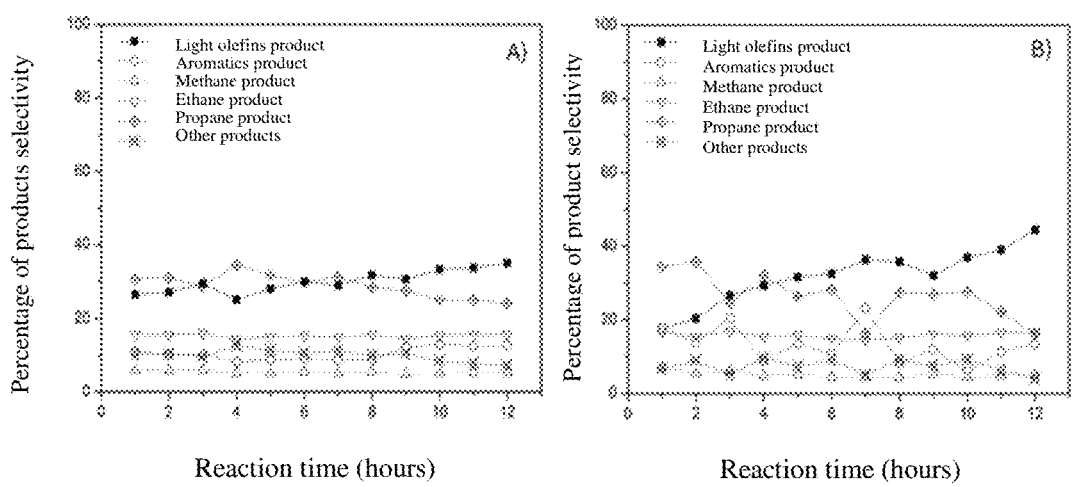
FIGS. 4 A) and B) show the light olefins product selectivity of the samples according to the invention Cat 1 and Cat 2 across times for the catalytic cracking of pentane respectively.

FIG. 4 shows the efficiency of light olefins product selectivity of the samples according to the invention that changed across the time. It was found that the catalyst according to the invention gave better efficiency than the comparative sample, wherein the sample according to the invention Cat 2 showed the highest pentane conversion and having higher light olefins product selectivity than other types of catalyst.

Figure 5:
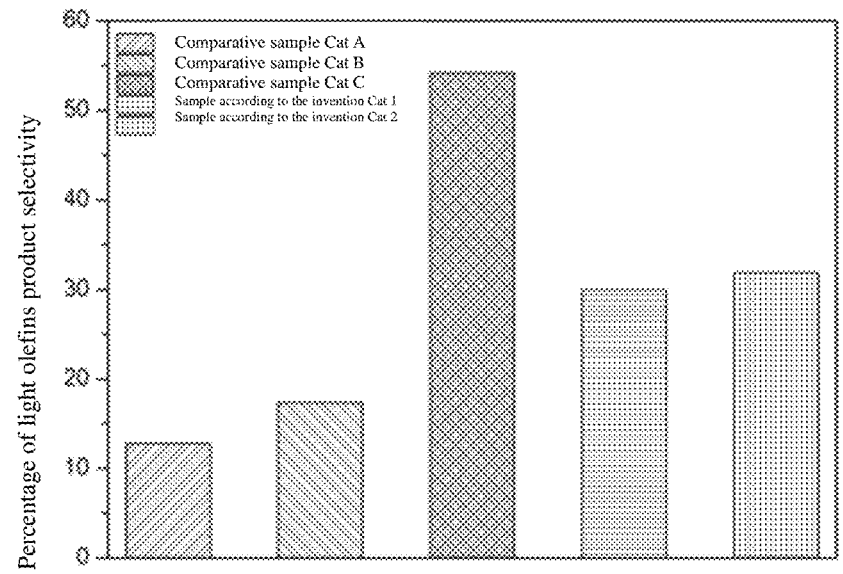
FIG. 5 shows the percentage of light olefins product selectivity of the samples according to the invention and the comparative samples for the catalytic cracking of pentane.

FIG. 5 shows the efficiency of light olefins product selectivity of the samples according to the invention and the comparative samples. It was found that the catalyst according to the invention gave better efficiency than the comparative samples, wherein sample according to the invention Cat 2 showed the higher pentane conversion and having higher light olefins product selectivity than other types of catalyst.

Figure 6:
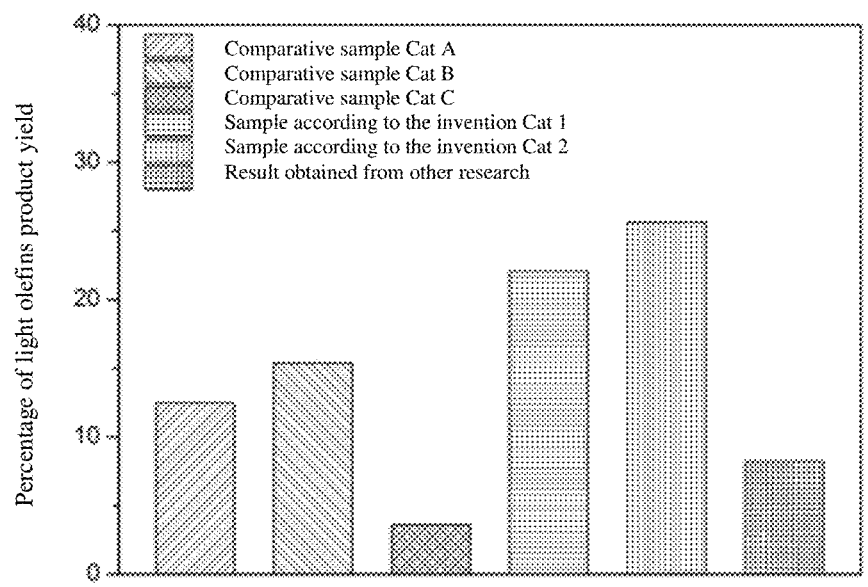
FIG. 6 shows the percentage of light olefins product yield of the samples according to the invention and the comparative samples for the catalytic cracking of pentane.

FIG. 6 shows the efficiency of light olefins product yield of the samples according to the invention and the comparative samples. It was found that the catalyst according to the invention gave better efficiency than the comparative samples, wherein the sample according to the invention Cat 2 showed the higher pentane conversion and having higher percent yield of light olefins product than other types of catalyst.

Figure 7:
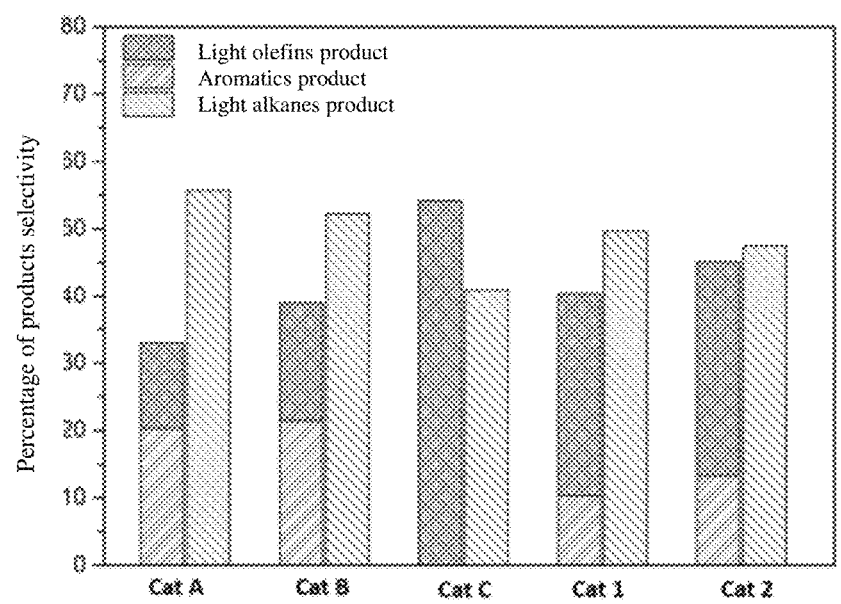
FIG. 7 shows the percentage of products selectivity of the samples according to the invention and the comparative samples for the catalytic cracking of pentane.

FIG. 7 shows the efficiency of the products selectivity of the samples according to the invention and the comparative samples. It was found that sample according to the invention Cat 2 showed the higher pentane conversion and having higher light olefins product selectivity than other types of catalyst, including having lower light alkane product selectivity.

From the results above, it can be said that the catalyst comprising the hierarchical zeolite core and the layered double hydroxide shell according to the invention gave high percent conversion of light olefins product yield and selectivity for the catalytic cracking of C4-C7 hydrocarbons as stated in the objective of this invention.

BEST MODE OF THE INVENTION

Best mode of the invention is as provided in the detailed description of the invention.

The invention claimed is:
1. A catalyst for producing light olefins from C4-C7 hydrocarbons, wherein said catalyst has a core-shell structure comprising a zeolite core with mole ratio of silicon to aluminium (Si/Al) between 2 to 250 and a layered double hydroxide shell and said zeolite is a hierarchical zeolite.

2. The catalyst according to claim 1, wherein said zeolite is the hierarchical zeolite comprising a micropore with size between 0.3 to 0.6 nm, a mesopore with size between 2 to 10 nm, and a macropore with size larger than 50 nm, wherein the mesopore and macropore proportions are greater than or equal to 15 to 60% when compared to a total pore volume.

3. The catalyst according to claim 1, wherein said zeolite has the mole ratio of silicon to aluminium between 15 to 30.

4. The catalyst according to claim 3, wherein said zeolite has the mole ratio of silicon to aluminium of equal to 15.

5. The catalyst according to claim 1, wherein said zeolite is selected from zeolite types ZSM-5, FAU, MOR, BETA or FER.

6. The catalyst according to claim 1, wherein said zeolite has a crystal size between 100 to 3,000 nm.

7. The catalyst according to claim 1, wherein the primary metals presented in said layered double hydroxide are the group 2 metals and the group 3 metals.

8. The catalyst according to claim 7, wherein the primary metals presented in said layered double hydroxide are magnesium (Mg) and aluminium (Al).

9. The catalyst according to claim 1, wherein said layered double hydroxide has a mole ratio of magnesium to aluminium between 1 to 3.

10. The catalyst according to claim 9, wherein said layered double hydroxide has the mole ratio of magnesium to aluminium between 1 to 2.

11. The catalyst according to claim 1, wherein said layered double hydroxide has a thickness between 100 to 1,000 nm.

12. The catalyst according to claim 1, wherein the catalyst comprises a core and a shell which has a mass ratio of shell:core between 1:1 to 1:7.

13. The catalyst according to claim 1, wherein the catalyst comprises a core and a shell which has a mass ratio of shell:core between 1:2 to 1:6.

14. A production process of light olefins from catalytic cracking reaction of C4-C7 hydrocarbons comprising: contacting C4-C7 hydrocarbons with a catalyst, wherein said catalyst has a core-shell structure comprising a zeolite core with mole ratio of silicon to aluminium (Si/Al) between 2 to 250 and a layered double hydroxide shell and said zeolite is a hierarchical zeolite.

15. The process according to claim 14, wherein said process is operated at temperature between 450 to 650° C. and pressure between atmospheric pressure 1 to 5 bars.

16. The process according to claim 14 or 15, wherein the C4-C7 hydrocarbons are selected from butane, pentane, hexane, or heptane.

17. The process according to claim 16, wherein the C4-C7 hydrocarbons are pentane.

18. The process according to claim 14, wherein the light olefins are ethylene and propylene.

* * * * *